(12) United States Patent
Kung et al.

(10) Patent No.: US 9,649,461 B2
(45) Date of Patent: May 16, 2017

(54) NESTED CANNULA STARTER ALIGNMENT

(71) Applicant: KONINKLIJKE PHILIPS N.V., Eindhoven (NL)

(72) Inventors: Cynthia Ming-Fu Kung, New York, NY (US); Karen Irene Trovato, Putnam Valley, NY (US)

(73) Assignee: Koninklijke Philips N.V., Eindhoven (NL)

( * ) Notice: Subject to any disclaimer, the term of this patent is extended or adjusted under 35 U.S.C. 154(b) by 158 days.

(21) Appl. No.: 14/387,604

(22) PCT Filed: Mar. 29, 2013

(86) PCT No.: PCT/IB2013/052539
§ 371 (c)(1),
(2) Date: Sep. 24, 2014

(87) PCT Pub. No.: WO2013/144914
PCT Pub. Date: Oct. 3, 2013

(65) Prior Publication Data
US 2015/0087899 A1    Mar. 26, 2015

Related U.S. Application Data

(60) Provisional application No. 61/617,764, filed on Mar. 30, 2012.

(51) Int. Cl.
*A61B 1/00* (2006.01)
*A61M 16/04* (2006.01)
(Continued)

(52) U.S. Cl.
CPC ..... *A61M 16/0488* (2013.01); *A61B 1/00045* (2013.01); *A61B 1/2676* (2013.01); *A61B 17/3421* (2013.01); *A61M 16/0427* (2014.02); *A61M 16/0434* (2013.01); *A61B 2017/00331* (2013.01); *A61B 2017/00455* (2013.01); *A61B 2017/00991* (2013.01);
(Continued)

(58) Field of Classification Search
CPC ............. A61B 1/00045; A61B 1/2676; A61M 16/0488
USPC ........................................ 600/103, 114, 117
See application file for complete search history.

(56) References Cited

U.S. PATENT DOCUMENTS 3,525,561 A * 8/1970 Takahashi .............. G02B 23/26
                                                         385/119
6,726,677 B1    4/2004 Flaherty
(Continued)

FOREIGN PATENT DOCUMENTS

WO    WO2007059233 A2    5/2007
WO    WO2008032230 A1    3/2008
(Continued)

*Primary Examiner* — Timothy J Neal

(57) ABSTRACT

A medical system includes a tube (102) configured to pass internally into a body and an index (108) disposed on the tube and configured to be visible internally within the tube. An outermost nested cannula (110) component is affixed within the tube with a geometric relationship with the tube as indicated by the index. An imaging device (106) is configured to image an anatomic reference relative to the index such that alignment of the outermost nested cannula component is provided by aligning the at least one index with the anatomic reference.

15 Claims, 4 Drawing Sheets

(51) Int. Cl.
    *A61B 1/267*   (2006.01)
    *A61B 17/34*   (2006.01)
    A61B 1/04      (2006.01)
    A61B 17/00     (2006.01)
    A61B 90/00     (2016.01)

(52) U.S. Cl.
    CPC . *A61B 2017/3443* (2013.01); *A61B 2090/069* (2016.02); *A61B 2090/0811* (2016.02); *A61B 2090/3937* (2016.02); *A61M 2210/1032* (2013.01)

(56) References Cited

U.S. PATENT DOCUMENTS

| | | |
|---|---|---|
| 2003/0199916 A1 | 10/2003 | Yee |
| 2012/0071714 A1* | 3/2012 | Jansen .................. A61B 1/005 600/104 |
| 2013/0023729 A1* | 1/2013 | Vazales ................ A61B 1/0669 600/104 |

FOREIGN PATENT DOCUMENTS

| | | | |
|---|---|---|---|
| WO | WO2009156892 A1 | 12/2009 | |
| WO | WO 2010/044051 A1 * | 4/2010 | ............... A61B 1/00 |
| WO | WO2010073135 A1 | 7/2010 | |
| WO | 2011126812 A1 | 10/2011 | |

* cited by examiner

US 9,649,461 B2

NESTED CANNULA STARTER ALIGNMENT

CROSS-REFERENCE TO PRIOR APPLICATIONS

This application is the U.S. National Phase application under 35 U.S.C. §371 of International Application Serial No. PCT/IB2013/052539, filed on Mar. 29, 2013, which claims the benefit of U.S. Application Ser. No. 61/617,764, filed on Mar. 30, 2012. These applications are hereby incorporated by reference herein.

This disclosure relates to medical devices and more particularly to nested cannulas or guides provided with a starter alignment device to provide a known alignment and position for a deployment of the nested cannula.

"Nested cannula" refers to a device constructed with nested, length-wise interlocking tubes, typically extended sequentially from largest to smallest. A commonly assigned pending application entitled "Nested Cannulae for Minimally Invasive Surgery", International Publication No. WO 2009/156892, Nov. 10, 2010, which is incorporated herein, in its entirety, discloses systems and methods for a nested cannula configuration to reach a target location within a particular anatomical region depending upon the requirements of the medical procedure. To employ a nested cannula by sequential deployment, the configuration of the tubes must be defined so that the path and the final pre-determined position of the distal tip may be achieved.

Nested cannulas are typically constructed based on a patient's 3D image to reach a particular target deep inside the patient, or are generated based on an atlas describing typical anatomy. The nested cannula needs to be oriented properly to be effective for its planned usage and to achieve its desired effect. Generally, a nested cannula must be at a particular position and orientation within a patient's body to reach a planned/predicted location upon being extended. Because individual have different physiological properties (e.g., physical dimensions), a same method for starting from outside the body to deploy a nested cannula generally cannot be employed on different individuals to reach a planned/predictable location for that individual. Further, an imaging system, such as a bronchoscope, can twist as it is deployed through an airway toward the lung and not provide a reliable starting position and/or orientation for the nested cannula. The imaging system, e.g., an endoscope, specifically, a bronchoscope may have imaging, lighting and frequently a working channel. An endo-tracheal (ET) tube may include a balloon for anchoring the tube.

In accordance with the present principles, a medical system includes a tube configured to pass internally into a body and an index disposed on the tube and configured to be visible internally within the tube. An outermost nested cannula component is affixed within the tube with a geometric relationship with the tube as indicated by the index. An imaging device is configured to image an anatomic reference relative to the index such that alignment of the outermost nested cannula component is provided by aligning the at least one index with the anatomic reference.

A medical system includes an initial alignment system for nested cannulas. The initial alignment system includes a tube configured to pass internally into a body, at least one index disposed on the tube and configured to be visible internally within the tube and an outermost nested cannula component affixed within the tube with a geometric relationship with the tube as indicated by the at least one index. An imaging device is configured to image an anatomic reference relative to the at least one index. A display device is configured to display the at least one index together with the anatomic reference to permit alignment of the outermost nested cannula component to control an initial deployment position of a nested cannula.

A method for deploying a medical instrument includes providing a tube configured to pass internally into a body, at least one index disposed on the tube and configured to be visible internally within the tube, an outermost nested cannula component affixed within the tube with a geometric relationship with the tube as indicated by the at least one index and an imaging device configured to image an anatomic reference relative to the at least one index; aligning the at least one index with the anatomic reference using an image of the at least one index with the anatomic reference to ensure an initial starting position of the outermost nested cannula component; and deploying a nested cannula from the initial starting position.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

The present embodiments provide systems, devices and methods for accurately locating a starting position for the deployment of a nested cannula device. The nested cannula should start at a particular position and orientation within the body. One problem is that different people have different physiologies, so the same method starting from a position outside the body cannot be used to reach a predictable location. The present embodiments provide a more universal starting position for the deployment of the nested cannula. A starting position system provides features that may include, e.g., a scope, such as a bronchoscope, an endo-tracheal (ET) tube having a deployable balloon to provide a particular position and orientation for starting the extension procedure of a nested cannula device/system to reach a planned/predicted target (deep) inside a particular patient. The ET tube is advanced until it reaches the carina, which is a fixed landmark of the lung although any other anatomical feature may be employed. The scope is inserted in and travels within the ET tube toward the carina or other anatomical feature. A mark, for example at both the top and bottom of the ET tube can be viewed through the scope. At the same time, the carina is also visible in the scope image, and the marks can be employed to align the ET tube with the carina. The ET tube can be rotated until the marks are parallel with the carina. The ET tube is then retracted a desired distance. The balloon on the ET may then be deployed to lock the position and orientation.

It should be understood that the present invention will be described in terms of medical instruments; however, the teachings of the present invention are much broader and are applicable to any instruments employed in repairing or analyzing complex biological or mechanical systems. In particular, the present principles are applicable to internal investigations and procedures for biological systems, procedures in all areas of the body such as the lungs, gastrointestinal tract, excretory organs, brain, heart, blood vessels, etc. The elements depicted in the FIGS. may be implemented in various combinations of hardware and may include software systems and provide functions which may be combined in a single element or multiple elements.

Figure 1:
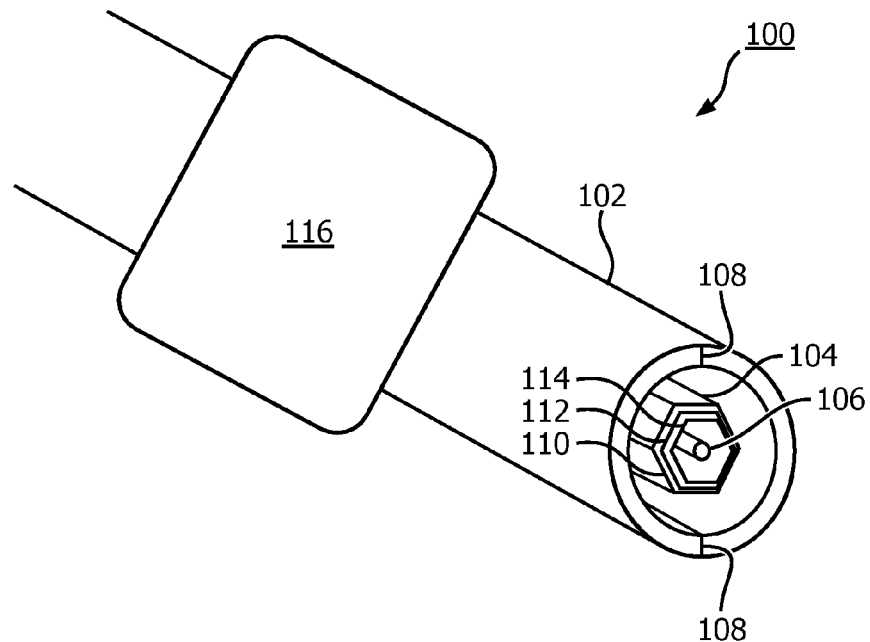
FIG. 1 is a perspective view of an initial alignment system in accordance with one illustrative embodiment.

Referring now to the drawings in which like numerals represent the same or similar elements and initially to FIG. 1, a system 100 for establishing a starting alignment position for a nested cannula is illustratively shown in accordance with one illustrative embodiment. System 100 includes an endo-tracheal (ET) tube (endobronchial tube or other tube) 102, which may include a deployable balloon 116 to lock in a particular position and/or orientation for starting an extension procedure of a nested cannula device/system 104 to reach a planned/predicted target inside a particular patient. The system 100 preferably includes an imaging system 106, e.g., a scope, such as a bronchoscope or the like. The imaging system or scope 106 may be inserted through the nested cannula 104 or may be inserted in the tube 102 outside of the outermost cannula tube 110. A mark or marks 108 (index) are placed on the tube 102 at strategic positions so that the marks 108 can be viewed in the scope image concurrently with anatomical features of a patient during the deployment of the system 100. For example, the marks 108 are located on opposite positions (e.g., a top and bottom) of the ET tube 102 and can be viewed through the scope 106.

The outer-most (largest) cannula tube 110 is affixed inside a tip of the ET tube 102, at a predetermined orientation, e.g., a fixed orientation that is maintained along the ET tube, specified by a nested cannula planner. The cannula tube 110 may be held in place using an adhesive (glue) or a mechanical device (e.g., a clip or other connecting mechanism). During a procedure, the ET tube 102 is advanced until it reaches an anatomical feature. In a particularly useful embodiment, the anatomical feature may include a carina, which is a fixed landmark (bifurcation) of the lung although any other anatomical feature may be employed. The scope 106 is inserted in or interlocked with the ET tube 102 and moved toward the carina or other anatomical feature.

Figure 2:
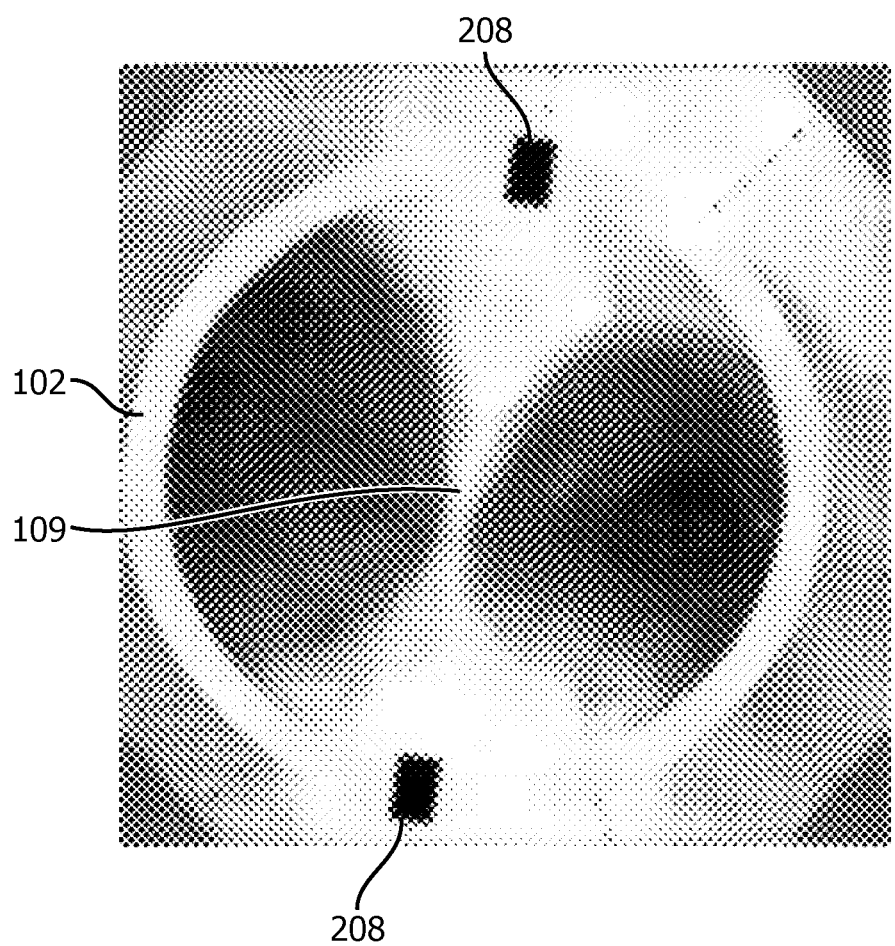
FIG. 2 is an image showing a carina aligned with marks disposed on an endo-tracheal (ET) tube in accordance with one illustrative embodiment.

Referring to FIG. 2, a carina 109 and the marks 108 on ET tube 102 are visible in a scope image as depicted. The marks 108 can be employed to align the ET tube 102 with the carina. For example, the ET tube 102 can be rotated until the marks 108 are parallel with the carina 109 or otherwise aligned with the carina 109. The ET tube 102 may then be retracted a desired distance while maintaining the proper orientation. The balloon 116 or other stabilizing device may now be deployed to lock the position and orientation of the ET tube 102.

Referring again to FIG. 1, the scope 106 is set at a specified distance from the tip of the ET tube 102, forming a combination scope/ET device. The nested cannula 104 is deployed by advancing cannula tubes 112 and 114 from within outermost tube 110. The cannula tubes 110, 112 and 114 may take on any shape and may include any number. FIG. 1 illustratively depicts three tubes 110, 112, 114; however, any number tubes may be employed.

Figure 3:
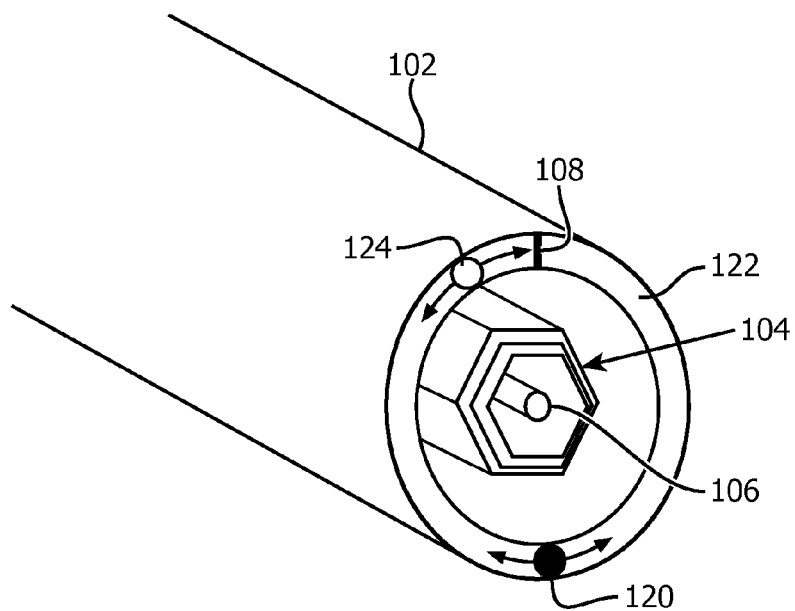
FIG. 3 is a perspective view of the initial alignment system of FIG. 1 having a gravity aligned component(s) provided on the ET tube in accordance with illustrative embodiments.

Referring to FIG. 3, the marks 108 may include indexes or shapes that are easily identified to determine a proper orientation of the ET tube 102. In one embodiment, the marks may include arrows (indicating up or down), letters ("t" for top, or "b" for bottom, etc.) or other indicia. Alternatively, a gravity aligned component may be employed to provide an orientation indicator. In one embodiment, a 'gravity' bead 120 may be employed and placed within a groove or race 122 along the ET tube's edge. The bead 120 may be employed to determine which side is "down", for example. The bead 120 may be employed along with indexes or marks 108 to provide alignment and position relative to a gravitational field. The race 122 should be fully enclosed to permit the bead or ball 120 to move therein but, the ball 120 should not be permitted to leave the enclosed race 120.

In another embodiment, bead 120 may be replaced by or may be employed with a bubble 124 or other component(s). In this example, the race 122 is fluid filled. In this way, the bubble 124 would float indicating an "up" position as opposed to a "down" position indicated by the bead 120. Other configurations are also contemplated. For example, multiple beads and bubbles may be employed or a bead and/or bubble may be employed with marks 108. In another embodiment, the enclosed race 122 may be filled with a first density liquid and a second liquid having a different density and a different color may be introduced. In this way, the colored density liquid may be employed instead of or in addition to the bead 120 or the bubble 124. The second liquid may include a food coloring or non-water soluble liquid, and the first density liquid may include water. Other materials may also be employed. The gravity aligned component (e.g., bead 120, bubble 124, different density liquids, etc.) assists in maintaining the set orientation, which may be needed if the ET tube 102 is retracted out of view of the carina. The ET tube 102 is then retracted a desired distance. The balloon 116 (FIG. 1) on the ET is then deployed to lock the position and orientation.

Figure 4:
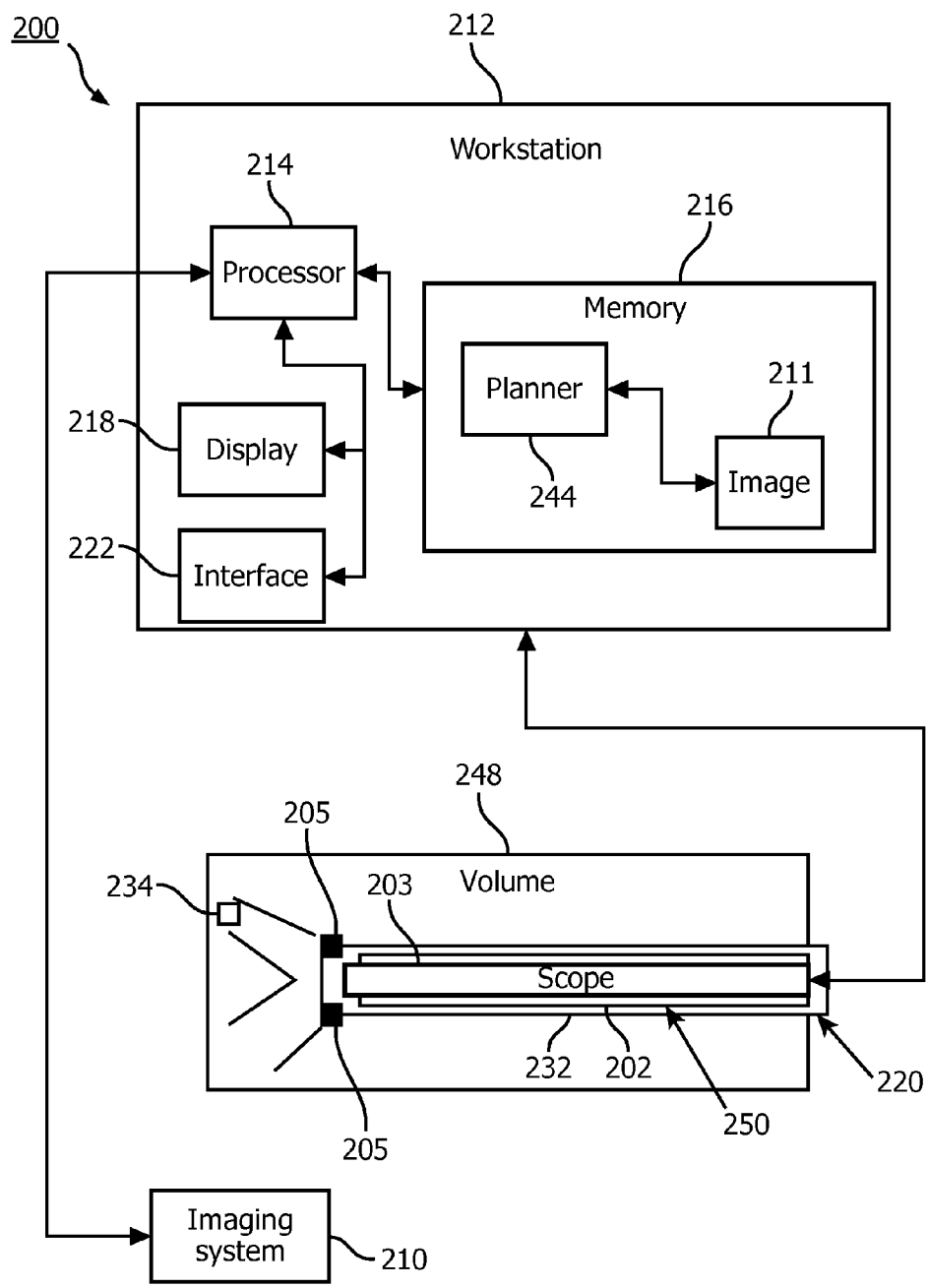
FIG. 4 is a block/flow diagram showing a system for performing a medical procedure in accordance with the present principles.

Referring to FIG. 4, a system 200 for designing and employing nested cannulas in accordance with the present principles is illustratively shown. The functions of the various elements shown in FIG. 4 can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

System 200 may include a workstation or console 212 from which a procedure is supervised and managed. Workstation 212 preferably includes one or more processors 214 and memory 216 for storing programs and applications. Memory 216 may store modules or software tools configured to interpret feedback signals or provide guidance and control of tools employed during a procedure. A planner 244 may be employed to design an instrument such as a nested cannula system 250, by providing arcs, lengths and orientations of cannula segments of the instrument 250 in a patient volume (e.g., an anatomical system) or a pathway system 248 (e.g., a pipe system, a wiring conduit, etc.).

The instrument 250 includes an outer cannula or tube 202 affixed within an ET tube 232. An imaging device or scope 203 is provided within the ET tube 232. The scope 203 provides images of a portion of the ET tube 232 and anatomical features so that a comparison and alignment process may be performed to align marks or indicia 205 with the anatomical feature or features. In one embodiment, the anatomical feature includes the carina. The scope 203, the ET tube 232 and at least the outermost cannula tube/component 202 will be referred to collectively as an initial alignment system 220. Workstation 212 may include a display 218 for viewing internal images of the subject 248 and the ET tube 232.

In one embodiment, an imaging system 210, such as a C-arm fluoroscopy system, is included whereby the images received may be compared to original computed tomography (CT) or other pre-operative images of a target 234 to validate reaching a final location. The imaging system 210 may include, e.g., a magnetic resonance imaging (MRI) system, a fluoroscopy system, a computed tomography (CT) system, ultrasound (US), etc. Display 218 may also permit a user to interact with the workstation 212 and its components and functions. This is further facilitated by an interface 222 which may include a keyboard, mouse, a joystick or any other peripheral or control to permit user interaction with the workstation 212.

Imaging system 210 may be provided for collecting pre-operative imaging data or realtime inter-operative imaging data. The pre-operative imaging may be performed at another facility, location, etc. in advance of any procedure. The imaging data may be stored as images 211 in memory 216, and may include pre-operative 3D image volumes of a patient or pathway system. Images 211 are preferably employed in designing the instrument 250, e.g., determining its dimensions and orientations for each nested portion for surgery and/or its deployment.

The target 234 may include a lesion, tumor, injury site, object, etc. During a procedure, the instrument 250 is deployed to reach the target 234. The nested cannula 250, its shapes, features and initial position are designed and configured in advance of a procedure based on input from the images 211 or an anatomical atlas. For example, the planner 244 employs the image and target data available for a specific patients' anatomy to plan the procedure and design the nested cannula 250, etc. to be proportioned with the other nested components so that it reaches the intended target 234. The angular position of the nested cannula 250 needs to be selected so that an initial alignment is provided. A patient-specific nested cannula can be simulated, approved, and delivered in a short period of time.

Exemplary embodiments of a nested cannula starter alignment system can be used to properly align and position a nested cannula device for each individual use. During a procedure, the initial alignment system 220 is deployed to a location, say in a lung. A position and orientation of the instrument 250 is determined based upon its design. An angular position of at least the outermost cannula tube 202 may be selected to give a desired orientation/predetermined position in accordance with the plan or design the instrument 250. This position is selected using marks 205 or other indicia located on the ET tube 232 and visible in an image of the scope 203. The marks 205 are employed to create a starting alignment for the nested cannula 250 to line up the marks with an anatomical reference (e.g., the carina) also present in the image of the scope 203.

Figure 5:
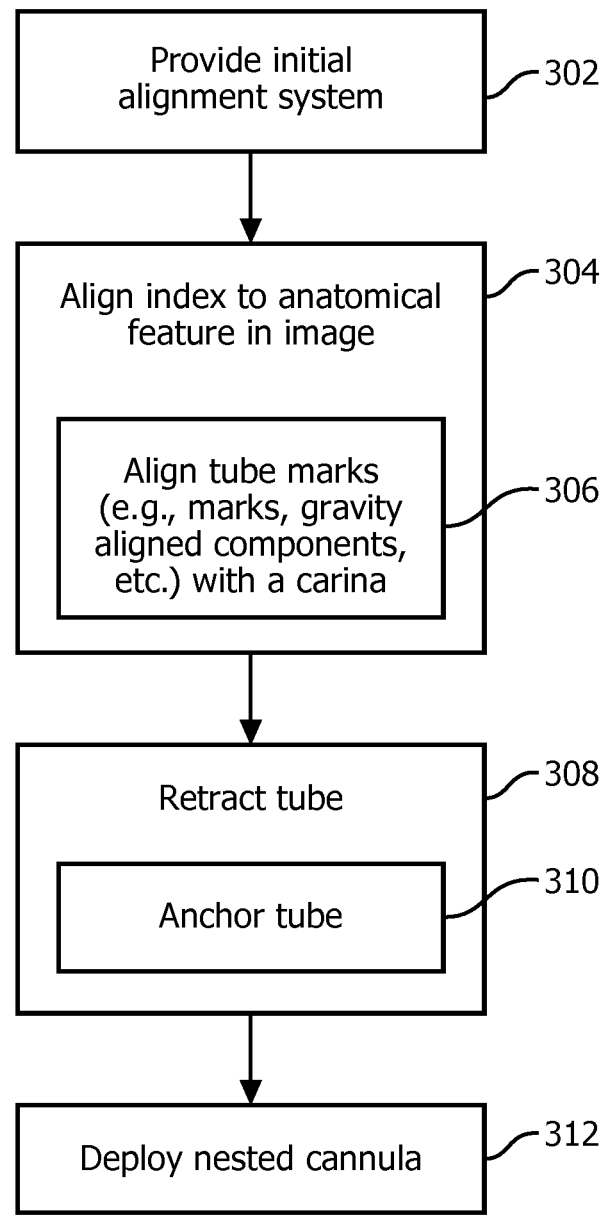
FIG. 5 is a flow diagram showing steps for performing a medical procedure in accordance with the present principles.

Referring to FIG. 5, a method for deploying a medical instrument is illustratively shown. In block 302, an initial alignment system is provided which includes a tube configured to pass internally into a body, and an index disposed on the tube and configured to be visible internally within the tube. An outermost nested cannula component is affixed within the tube with a geometric relationship with the tube as indicated by the index, and an imaging device configured to image an anatomic reference relative to the at least one index.

In block 304, the index is aligned with the anatomic reference using an image of the index and the anatomic reference concurrently shown to ensure an initial starting position of the outermost nested cannula component. In one embodiment, the index may include diametrically opposed marks on the tube. The tube may include an endo-tracheal tube or bronchoscope, and the anatomic reference may include a carina. In block 306, the diametrically opposed marks on the tube are aligned with the carina. In one embodiment, one of the marks may include a bubble, gravity bead or other orientation providing arrangement (e.g., magnetic particles to indicate a magnetic position, etc.).

In block 308, the tube may be retracted a predetermined amount to permit deployment of the nested cannula. In block 310, the tube may be anchored after the retraction to maintain its position. The anchoring may include employing a balloon or other device to stabilize and anchor the tube position. In block 312, a nested cannula is deployed from the initial starting position. This properly aligns the deployment of the nested cannula to ensure that a target is reached.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for nested cannula starter alignment systems, devices and methods (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A medical system, comprising:
a tube configured to pass internally into a body;
at least one index disposed on the tube and configured to be visible internally within the tube;
a nested cannula having a plurality of nested cannula components, said nested cannula including an outermost nested cannula component affixed within the tube with a geometric relationship with the tube as indicated by the at least one index; and
an imaging device configured to image an anatomic reference relative to the at least one index such that alignment of the outermost nested cannula component is provided by aligning the at least one index with the anatomic reference.

2. The system as recited in claim 1, wherein the at least one index includes diametrically opposed marks on the tube.

3. The system as recited in claim 1, wherein the imaging device includes an endoscope.

4. The system as recited in claim 3, wherein the endoscope is located within the outermost cannula component.

5. The system as recited in claim 3, wherein the endoscope is located within the tube outside the outermost cannula component.

6. The system as recited in claim 1, wherein the tube includes an endo-tracheal tube and the anatomic reference includes a carina.

7. The system as recited in claim 1, wherein the tube includes a gravity aligned component to orient the tube and provide a reference during a procedure.

8. The system as recited in claim 7, wherein the gravity aligned component includes one or more of a gravity bead, a bubble and/or different density liquids.

9. A medical system, comprising:
an initial alignment system including:
a tube configured to pass internally into a body;
at least one index disposed on the tube and configured to be visible internally within the tube;
a nested cannula having a plurality of nested cannula components, said nested cannula including an outermost nested cannula component affixed within the tube with a geometric relationship with the tube as indicated by the at least one index; and
an imaging device configured to image an anatomic reference relative to the at least one index; and
a display device configured to display the at least one index together with the anatomic reference to permit alignment of the outermost nested cannula component to control an initial deployment position of a nested cannula.

10. The system as recited in claim 9, wherein the at least one index includes diametrically opposed marks on the tube.

11. The system as recited in claim 9, wherein the imaging device includes an endoscope.

12. The system as recited in claim 11, wherein the endoscope is located within the outermost cannula component.

13. The system as recited in claim 11, wherein the endoscope is located within the tube outside the outermost cannula component.

14. The system as recited in claim 9, wherein the tube includes an endo-tracheal tube and the anatomic reference includes a carina.

15. The system as recited in claim 9, wherein the tube includes a gravity aligned component to orient the tube and provide a reference during a procedure.

* * * * *